(12) United States Patent
Duan et al.

(10) Patent No.: US 10,869,811 B2
(45) Date of Patent: Dec. 22, 2020

(54) PHYSIOTHERAPY DEVICE AND METHOD FOR CONTROLLING THE PHYSIOTHERAPY DEVICE

(71) Applicant: Ankon Medical Technologies (Shanghai), LTD., Shanghai (CN)

(72) Inventors: Xiaodong Duan, Pleasanton, CA (US); Pengsong Ji, Beijing (CN)

(73) Assignee: ANKON MEDICAL TECHNOLOGIES (SHANGHAI), LTD., Shanghai (CN)

( * ) Notice: Subject to any disclaimer, the term of this patent is extended or adjusted under 35 U.S.C. 154(b) by 713 days.

(21) Appl. No.: 15/058,216

(22) Filed: Mar. 2, 2016

(65) Prior Publication Data

US 2016/0310357 A1  Oct. 27, 2016

(30) Foreign Application Priority Data

Apr. 27, 2015  (CN) .......................... 2015 1 0207015

(51) Int. Cl.
| | | |
|---|---|---|
| *A61H 23/00* | (2006.01) | |
| *A61H 23/02* | (2006.01) | |
| *A61N 2/12* | (2006.01) | |
| *A61N 2/00* | (2006.01) | |

(52) U.S. Cl.
CPC ......... *A61H 23/0263* (2013.01); *A61N 2/002* (2013.01); *A61N 2/12* (2013.01); *A61H 2023/0281* (2013.01); *A61H 2201/10* (2013.01); *A61H 2201/1215* (2013.01); *A61H 2201/5005* (2013.01); *A61H 2201/5007* (2013.01); *A61H 2201/5023* (2013.01); *A61H 2201/5035* (2013.01); *A61H 2201/5058* (2013.01)

(58) Field of Classification Search
CPC ........ A61H 23/0263; A61H 2201/5058; A61H 2201/5035; A61H 2201/10; A61H 2201/5007; A61H 2201/1215; A61H 2201/5023; A61N 2/12; A61N 2/002
See application file for complete search history.

(56) References Cited

U.S. PATENT DOCUMENTS

| | | | | |
|---|---|---|---|---|
| 4,239,040 A | * | 12/1980 | Hosoya .................. | A61B 10/02 600/582 |
| 5,562,706 A | * | 10/1996 | Lauterbach ............ | A61N 1/328 607/3 |
| 9,078,799 B2 | | 7/2015 | Shohat et al. | |
| 9,155,677 B2 | | 10/2015 | Lacy | |
| 9,717,376 B2 | * | 8/2017 | Hwang .................. | A61H 7/005 |

(Continued)

FOREIGN PATENT DOCUMENTS

| | | |
|---|---|---|
| AU | 2007298473 | 3/2008 |
| AU | 2014224165 | 10/2017 |

(Continued)

*Primary Examiner* — Quang D Thanh
(74) *Attorney, Agent, or Firm* — Treasure IP Group, LLC

(57) ABSTRACT

A physiotherapy device and a method for controlling the physiotherapy device are provided. The physiotherapy device includes a vibration capsule. The vibration capsule further includes a shell, a vibration motor being placed in the shell, a control panel connecting with the vibration motor electrically, and one or more batteries connecting with the vibration motor and the control panel electrically. The vibration motor includes a rotor closed to an end of the shell and a rotary magnet fixed on the rotor.

8 Claims, 6 Drawing Sheets

(56) References Cited

U.S. PATENT DOCUMENTS

| | | | |
|---|---|---|---|
| 2005/0079132 A1* | 4/2005 | Wang | A61L 31/082 424/1.11 |
| 2006/0169293 A1* | 8/2006 | Yokoi | A61B 1/00156 128/899 |
| 2006/0255665 A1* | 11/2006 | Kraus | H02K 33/18 310/36 |
| 2007/0123809 A1 | 5/2007 | Weiss | |
| 2009/0318841 A1* | 12/2009 | Shohat | A61H 23/0263 601/46 |
| 2012/0010688 A1* | 1/2012 | Lamb | A61F 7/00 607/103 |
| 2013/0066304 A1* | 3/2013 | Belson | A61B 17/00234 606/1 |
| 2014/0081169 A1* | 3/2014 | Gerding | A61B 1/015 600/560 |
| 2014/0088462 A1* | 3/2014 | Mishelevich | A61N 2/006 601/2 |
| 2014/0142472 A1* | 5/2014 | Giraud | A61H 7/005 601/18 |
| 2015/0073315 A1* | 3/2015 | Shabbat | A61B 1/00156 601/46 |
| 2015/0313792 A1 | 11/2015 | Shohat et al. | |
| 2016/0136037 A1* | 5/2016 | Cai | A61H 19/34 601/46 |
| 2016/0352185 A1* | 12/2016 | Weiss | H04M 19/047 |

FOREIGN PATENT DOCUMENTS

| | | | |
|---|---|---|---|
| CN | 201194905 | 2/2009 | |
| CN | 201211317 | 3/2009 | |
| CN | 201642791 | 11/2010 | |
| CN | 1994255 | 2/2011 | |
| CN | 101984947 | 3/2011 | |
| CN | 101999976 | 4/2011 | |
| CN | 1981729 | 6/2011 | |
| CN | 101511305 | 5/2012 | |
| CN | 101516314 | 5/2014 | |
| CN | 204655456 | 9/2015 | |
| CN | 105079970 | 11/2015 | |
| DE | 10121191 C1 * | 9/2002 | A61N 2/00 |
| EP | 2073779 | 7/2009 | |
| EP | 1906830 | 9/2013 | |
| EP | 2814376 | 12/2014 | |
| JP | 2011045723 | 3/2011 | |
| WO | 2008035329 | 3/2008 | |
| WO | 2013121276 | 8/2013 | |

* cited by examiner

PHYSIOTHERAPY DEVICE AND METHOD FOR CONTROLLING THE PHYSIOTHERAPY DEVICE

CROSS-REFERENCE TO RELATED APPLICATIONS

This application claims priority to Chinese Patent Application No. 201510207015.X filed on Apr. 27, 2015, the contents of which are incorporated by reference herein.

FIELD OF THE INVENTION

The subject matter herein generally relates to a massage device, and particularly to a physiotherapy device and a method for controlling the physiotherapy device.

BACKGROUND

An increasing number of people suffer overweight or constipation. A drug having a cathartic effect is always used for losing weight or avoiding constipation. If a drug is used by a user for a long time, it may lead to a dependency on the drug, and a side effect of dehydration may become an issue for the user. Moreover, a message device in vitro has been developed for losing weight or avoiding constipation. However, the effect of the message device is decreased by internal abdominal fat. Therefore, a physiotherapy device in vivo and a method for controlling the physiotherapy device are needed.

BRIEF DESCRIPTION OF THE DRAWINGS

Implementations of the present technology will now be described, by way of example only, with reference to the attached figures.

DETAILED DESCRIPTION

Figure 1:
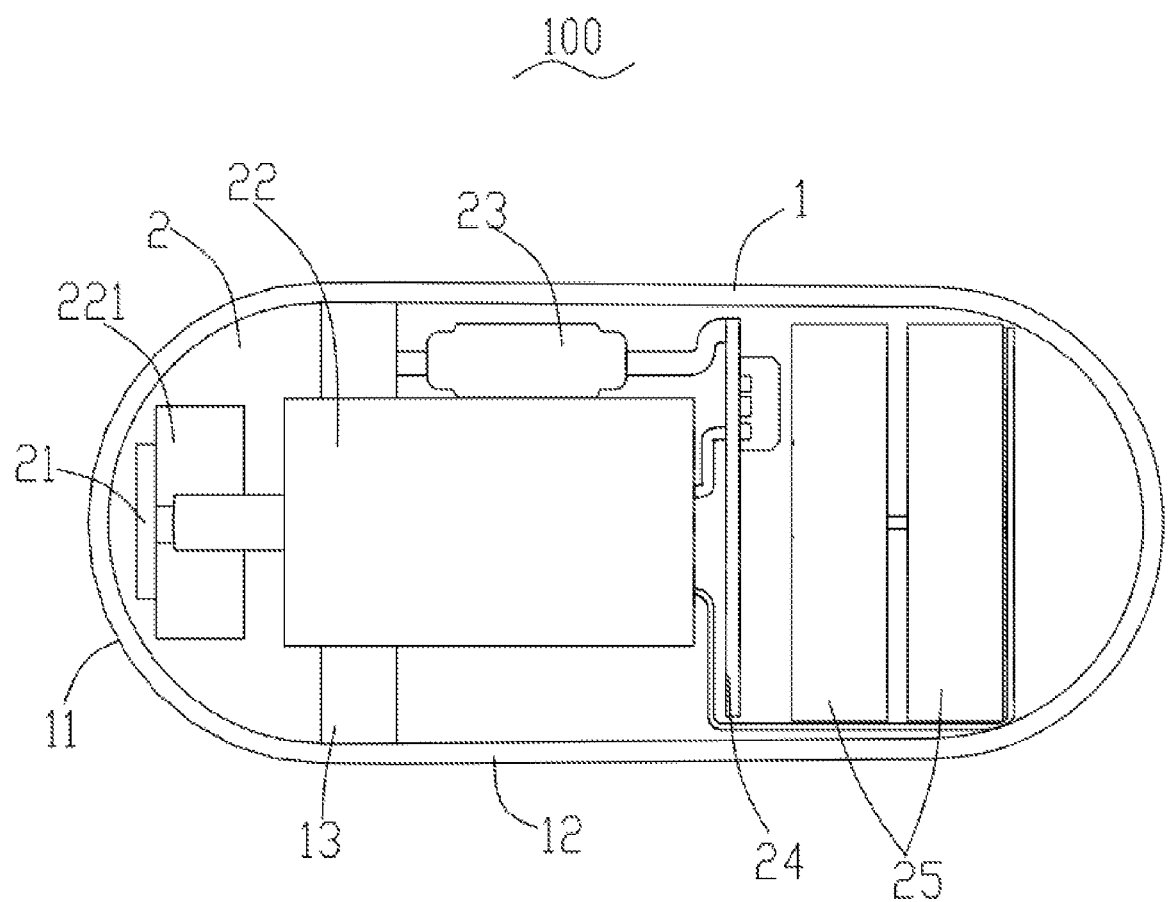
FIG. 1 is a diagram of one example embodiment of a vibration capsule of a physiotherapy device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure are presented as the follows.

The term "module" refers to logic embodied in computing or firmware, or to a collection of software instructions, written in a programming language, such as, Java, C, or assembly. One or more software instructions in the modules may be embedded in firmware, such as in an erasable programmable read only memory (EPROM). The modules described herein may be implemented as either software and/or computing modules and may be stored in any type of non-transitory computer-readable medium or other storage device. Some non-limiting examples of non-transitory computer-readable media include CDs, DVDs, BLU-RAY, flash memory, and hard disk drives. The term "comprising" means "including, but not necessarily limited to;" it specifically indicates open-ended inclusion or membership in a so-described combination, group, series and the like.

Figure 2:
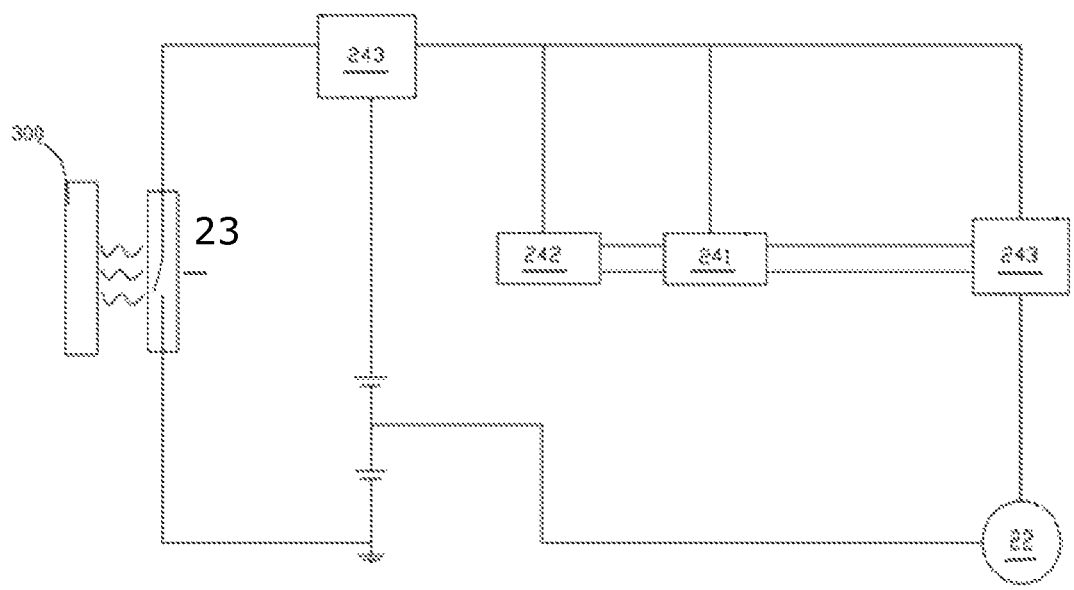
FIG. 2 is a block diagram of the example embodiment of a control circuit of the physiotherapy device.

FIGS. 1-2 are a diagram of one example embodiment of a physiotherapy device. The physiotherapy device can comprise a vibration capsule 100 and a magnetic base 300 matching with the vibration capsule 100. In at least one embodiment, the magnetic base 300 can comprise a bottom base (not shown in FIGS. 1-2) for seating the vibration capsule 100, a configuration device of magnetic field (not shown in FIGS. 1-2) for configuring operations of the vibration capsule 100, and a magnetic component (not shown in FIGS. 1-2) for turning on or turning off the vibration capsule 100.

In at least one embodiment, the vibration capsule 100 comprises a shell 1, and the shell 1 comprises a body 12 in hollow cylinder and two hemispheric heads 11 connecting with two ends of the body 12. The shell 1 can be a biocompatibility shell, which can be eaten by users and does not produce ill-effect. The biocompatibility shell also can not be absorbed by the users, and can protect components in the shell 1 from being corroding.

An enclosed space 2 is formed in internal of the body 12 and the two hemispheric heads 11. In at least one embodiment, the enclosed space 2 comprises a vibration motor 22, a control panel 24 connecting with the vibration motor 22 electrically, a reed switch 23 connecting with the vibration motor 22 and the control panel 24 electrically, and one or more batteries 25 connecting with the vibration motor 22 and the control panel 24 electrically. The vibration motor 22, the control panel 24 and the one or more batteries 25 are placed in sequence in the enclosed space 2 along the axial direction of the shell 1.

In at least one embodiment, a fan holder 13 is placed in the body 12. The fan holder 13 can be placed perpendicular to the horizontal axis of the shell 1 and be placed close to a hemispheric head 11. The fan holder 13 also resists interior of the body 12. The fan holder 13 is used to fix the vibration motor 22.

In at least one embodiment, the vibration motor 22 can be a column-shaped motor. One end of the vibration motor 22 goes through the fan holder 13, and the vibration motor 22 is fixed by the fan holder 13. The fan holder 13 can fix the vibration motor 22 and can resist interior of the body 12 to keep the shape of the vibration capsule 100 from being changing. In at least one embodiment, the vibration motor 22 can comprise a rotor 221, and the rotor 221 of the vibration motor 22 can be placed closed to a hemispheric head 11, which is far away from the one or more batteries for improving the effect of vibration. The fan holder 13 is placed closed to the end of the rotor 221 of the vibration motor 22.

In at least one embodiment, the vibration motor 22 further comprises a rotary magnet 21. The rotary magnet 21 can be fixed on a surface of the rotor 221, which is far away from the one or more batteries 25, or can be fixed on a lateral surface of the rotor 221. The lateral surface of the rotor 221 is an upper surface or a lower surface of the rotor 221, which is in parallel with the horizontal axis of the vibration capsule 100. The rotary magnet 21 can rotate along with the rotor 221 to form a rotation magnetic field. The range of the magnetic field of the rotary magnet 21 can be set as a value from 0.06 T to 0.5 T.

Figure 3:
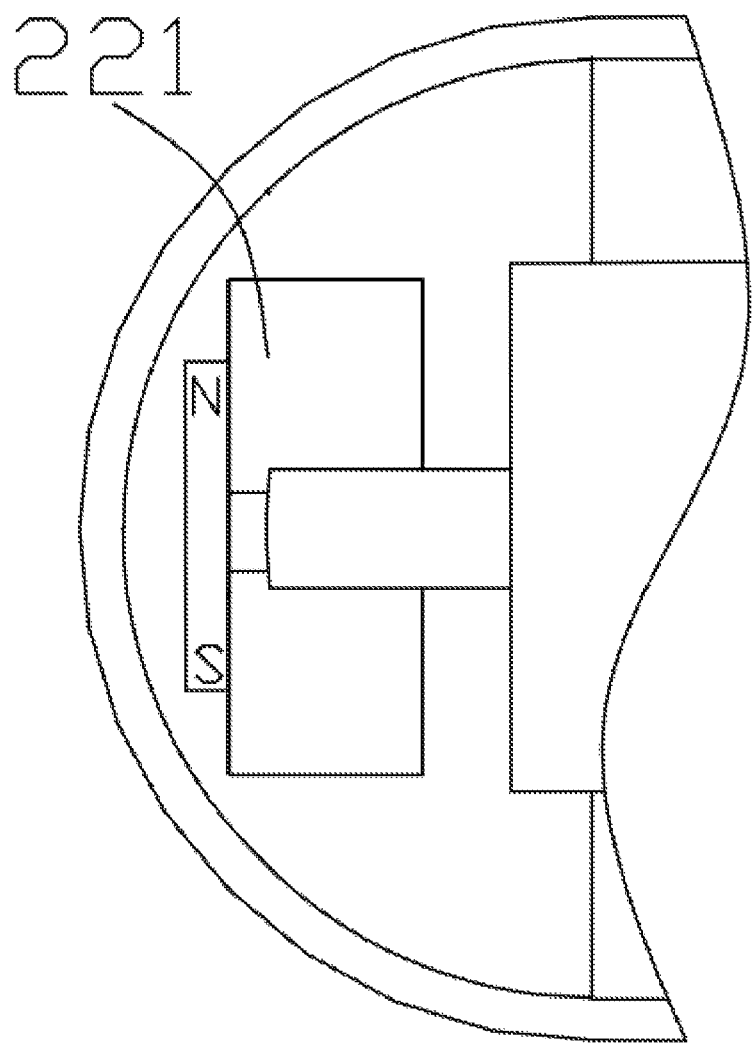
FIG. 3 is a partial diagram of the example embodiment of the vibration capsule in FIG. 1.
Figure 4:
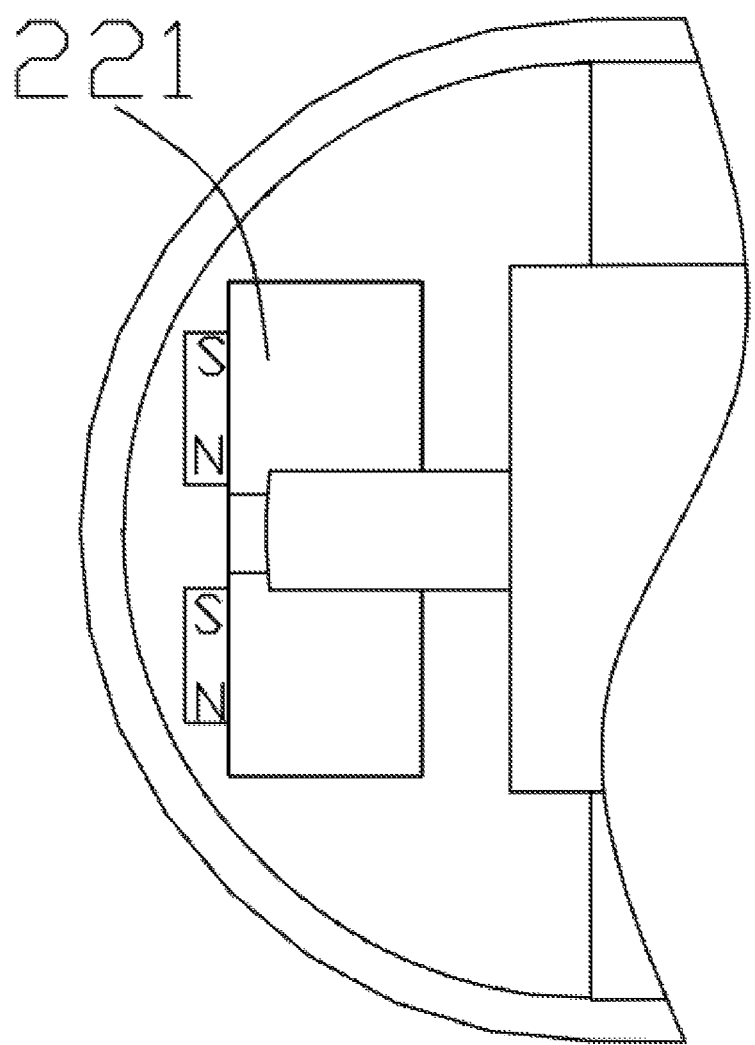
FIG. 4 is a partial diagram of a second example embodiment of the vibration capsule in FIG. 1 for displaying at least two magnet bodies of a rotary magnet in the same direction of poles.
Figure 5:
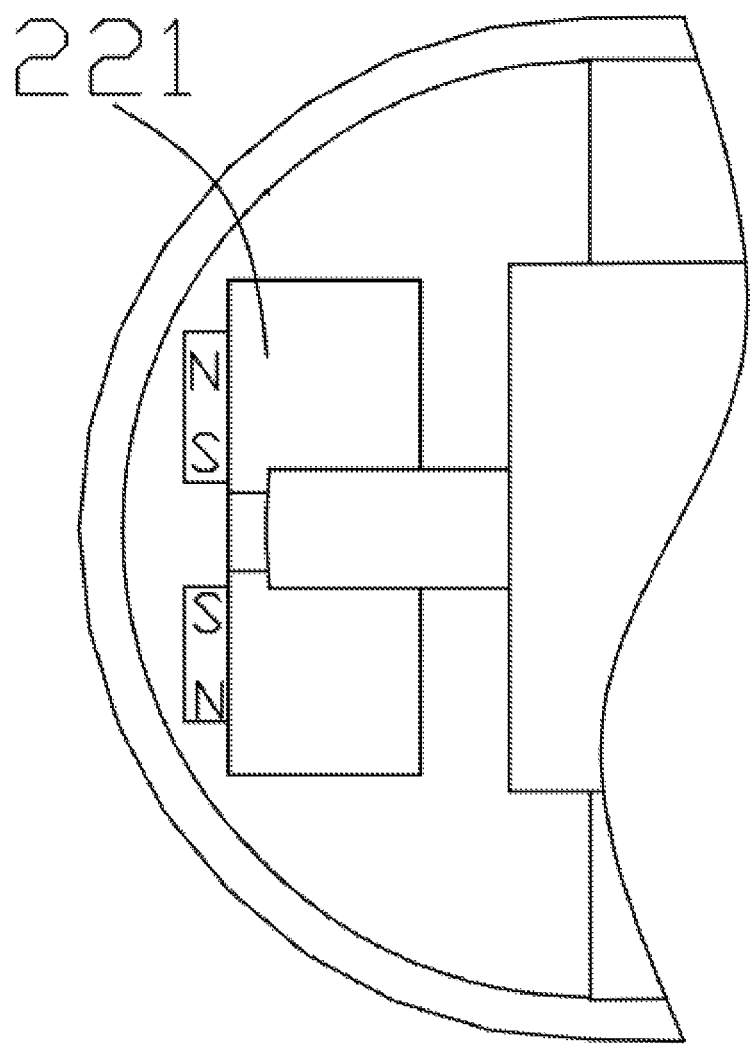
FIG. 5 is a partial diagram of a third example embodiment of the vibration capsule in FIG. 1 for displaying at least two magnet bodies of a rotary magnet in the reverse direction of poles.

As illustrations shown in FIGS. 3-5, the rotary magnet 21 comprises at least one magnetic body, and poles of two adjacent magnetic bodies are placed in the same direction or in the reverse direction when the rotary magnet 21 comprises at least two magnetic bodies. As the illustration shown in FIG. 3, the rotary magnet 21 comprises one magnetic body. As the illustration shown in FIG. 4, the rotary magnet 21 comprises at least two magnetic bodies (e.g., a quantity of M, and M is an integer that is not less than 2), and poles of the at least two magnetic bodies are placed in the same direction. As the illustration shown in FIG. 5, the rotary magnet 21 comprises at least two magnetic bodies (e.g., a quantity of N, and N is an integer that is not less than 2), and poles of two adjacent magnetic bodies are placed in the reverse direction. The illustration shown in FIG. 5 can be set as a preferred illustration of the embodiment. When poles of the N magnetic bodies are placed in the reverse direction between two adjacent magnetic bodies, the change frequency of the rotation magnetic field of the rotary magnet 21 is N/2 times of a magnetic body, and the attenuation of the rotation magnetic field of the rotary magnet 21 can be adjusted according to the distances between two adjacent magnetic bodies. The attenuation of the rotation magnetic field of the at least two magnetic bodies is slower than the rotation magnetic field of a magnetic body. The magnetic body can be, but is not limited to, a NdFeB magnet, a ferroferric oxide, or a cobalt-nickel.

Figure 6:
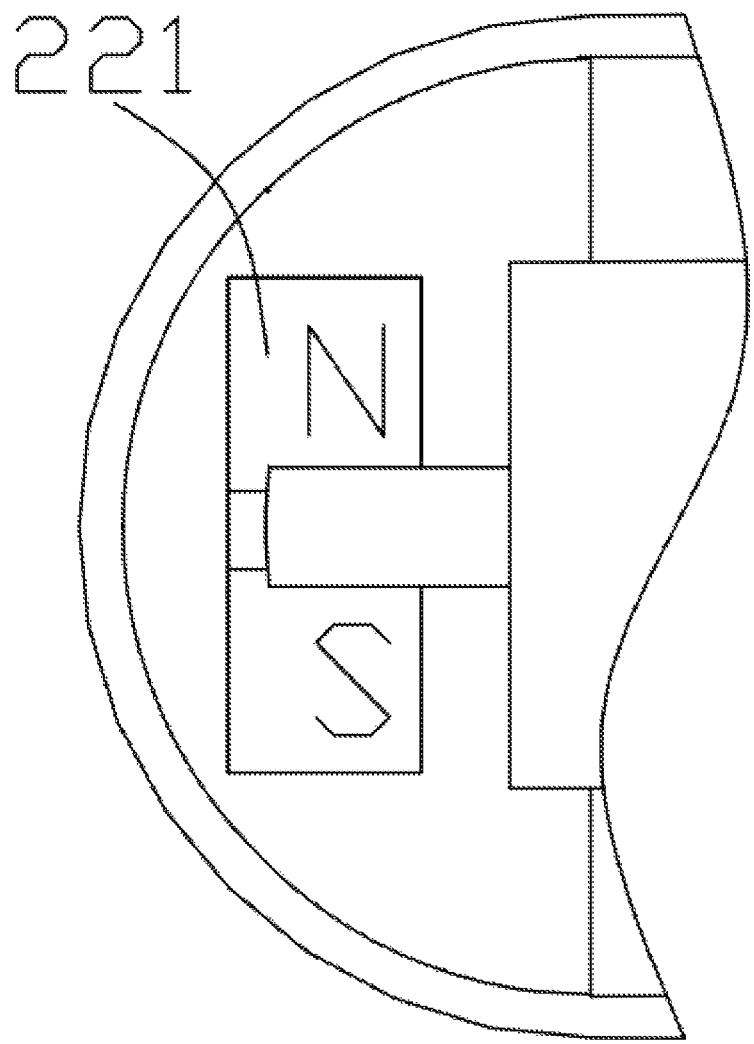
FIG. 6 is a partial diagram of a fourth example embodiment of the vibration capsule in FIG. 1.

As an illustration shown in FIG. 6, the rotor 221 and the rotary magnet 21, are replaced by a magnetic rotor, and the magnetic rotor is placed on the vibration motor 22 to form the rotation magnetic field. The range of the magnetic field of the magnetic rotor also can be set as a value from 0.06 T to 0.5 T.

The rotation magnetic field can produce a magnetic stimulation to digestive tract of users in an impulse type. The rotation magnetic field can stimulate the circulation of blood, adjust blood pressure, develop immunity from disease, and get rid of fatigue. Therefore, the physiotherapy device can achieve a good physiotherapeutic result by placing the rotary magnet 21 on the rotor 221 or using the magnetic rotor to form the rotation magnetic field.

The rotation speed of the rotor 221 can be set as, but is not limited to, a value from 100 revolutions per minute (r/min) to 15000 r/min. The rotation speed of the rotor 221 can be set according to gastrointestinal function of users. Slow rotation speed of the rotor 221 (e.g., less than 2000 r/min) can be set for the user who has a poor gastrointestinal function (e.g., old people or children). Quick rotation speed of the rotor 221 (e.g., larger than 10000 r/min and less than 15000 r/min) can be set for the user who has a good gastrointestinal function. The vibration motor 22 can adjust the rotation speed of the rotor 221 according to the gastrointestinal function of users to achieve resonance for getting a best vibration effect.

As an illustration shown in FIG. 2, the control panel 24 can comprise a microprocessor 241, a magnetic sensor 242 and a current amplification chip 243. The microprocessor 241 is used for programming the working mode of the vibration motor 22. The current amplification chip 243 is used for amplifying current signals of the control panel 24.

As illustrations shown in FIGS. 1-2, the reed switch 23 connecting with the control panel 24 electrically. An end of the reed switch 23 is fixed on the fan holder 13, and another end of the reed switch 23 is fixed on the control panel 24. The reed switch 23 is placed between the vibration motor 22 and the body 12 of the shell 1, and is placed closed to interior of the body 12 for matching with the magnetic component of the magnetic base 300 to turn on or turn off the vibration capsule 100 conveniently. When the magnetic component of the magnetic base 300 is closed to the reed switch 23 in a predetermined range, internal reed of the reed switch 23 is pushed to disconnect circuits of the control panel 24, and the vibration capsule 100 is turned off by the magnetic component of the magnetic base 300. The predetermined range is determined according to the magnetic strength of the magnetic component. When the magnetic component of the magnetic base 300 is away from the reed switch 23 in the predetermined range, the internal reed of the reed switch 23 is pulled to connect circuits of the control panel 24, and the vibration capsule 100 is turned on by the magnetic component of the magnetic base 300. The magnetic force of the magnetic component is larger than the magnetic force of the rotary magnet 21.

In at least one embodiment, two series batteries 25 are placed on the control panel 24, which is away from the vibration motor 22. The two series batteries 25 are used for providing electricity to power the control panel 24 and the vibration motor 22.

The physiotherapy device programs the working mode of the vibration motor 22 by using the microprocessor 241. The working mode of the vibration motor 22 woks as follows.

Step S1, the microprocessor 241 turns on the vibration capsule 100.

Step S2, the microprocessor 241 controls the vibration motor 22 to vibrate between 5 seconds to 15 seconds for testing whether the vibration motor 22 can work normally.

Step S3, the microprocessor 241 controls the vibration motor 22 to enter sleeping mode for a default time. The default time is user-determined or pre-determined by the users, for example, six hours are preferred.

Step S4, the microprocessor 241 controls the vibration motor 22 to vibrate according to the rotation speed of the rotor 221 after the default time.

Step S5, the microprocessor 241 controls the vibration motor 22 to stop working when electricity of the one or more batteries 25 is exhausted.

The working mode of the vibration motor 22 also can be configured by the configuration device of magnetic field of the magnetic base 300 before the vibration motor 22 is turned on. In at least one embodiment, the configuration device of magnetic field configures working mode of the vibration motor 22 from step S2 to step S4 according to working requirements of the vibration motor 22. The magnetic sensor 242 acquires the working mode of the vibration motor 22 from the configuration device of magnetic field and sends the working mode of the vibration motor 22 to the microprocessor 241. The microprocessor 241 controls the vibration motor 22 to vibrate according to the working mode.

When electricity of the one or more batteries 25 is exhausted, the vibration motor 22 stops working and the vibration motor 22 can be excreted from the body of users with stools.

During the manufacturing process of the vibration capsule 100, the vibration motor 22, the reed switch 23, the microprocessor 241, the current amplification chip 243 and the magnetic sensor 242 are welded on a default position of the control panel 24. The vibration motor 22, the microprocessor 241, the current amplification chip 243, the magnetic sensor 242 and the reed switch 23 are connected electrically according to the connections of FIG. 2. The electrical connections are test for determining whether the electrical connections are right. After the electrical connections are right, the working mode of the vibration motor 22 is programmed to the microprocessor 241. After the vibration capsule 100 is packaged, the vibration capsule 100 is placed on the magnetic base 300 to obtain the physiotherapy device.

In the present invention, the physiotherapy device can be used to lose weight or avoid constipation by the vibration of the vibration motor 22. Moreover, the rotation magnetic field can produce magnetic stimulation to digestive tract of users in an impulse type for stimulating the circulation of blood of the users.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A physiotherapy device comprising:
    a vibration capsule, configured to navigate through a digestive track of a patient and to reduce constipation, the vibration capsule comprising:
        a shell configured to protect components in the shell from being corroding;
        a column-shaped vibration motor set in the shell;
        a control panel connecting with the column-shaped vibration motor electrically;
        one or more batteries connecting with the column-shaped vibration motor and the control panel electrically; and
        a fan holder, placed in the shell, being perpendicular to a horizontal axis of the shell and, configured to secure the column-shaped vibration motor closer to a hemispheric head of the shell and to keep a shape of the vibration capsule from being changed, and wherein the fan holder is placed close to an end of a rotor of the column-shaped vibration motor;
    wherein the column-shaped vibration motor comprising:
        the rotor disposed close to the hemispheric head of the shell, and
        a rotary magnet fixed on the rotor, configured to create a rotational magnetic field in the digestive track of the patient,
            wherein the rotary magnet comprises a plurality number N of magnetic bodies, while N being an integer not less than 2, having a first magnetic body separated from its adjacent magnetic body by a distance, and poles of the first magnetic body and its adjacent magnetic body are placed in a reverse direction;
        the distance between the first magnetic body and its adjacent magnetic body is varied thereby adjusting an attenuation of the rotational magnetic field of the rotary magnet; and a change in an attenuation of rotational magnetic field of the plurality of magnetic bodies is milder than a change in rotational magnetic field of the first magnetic body, wherein a range of the rotational magnetic field of the rotary magnet is set as a value from 0.06 T to 0.5 T;
    wherein the control panel comprises a microprocessor for programming working mode of the column-shaped vibration motor, a magnetic sensor, and a current amplification chip; and
    wherein a rotation speed of the rotor is set as a value from 100 revolutions per minute to 15000 revolutions per minute.

2. The physiotherapy device according to claim 1, wherein the column-shaped vibration motor, the control panel and the one or more batteries are placed in sequence along an axial direction of the shell.

3. The physiotherapy device according to claim 1, wherein the rotary magnet is fixed on a surface of the rotor which is far away from the one or more batteries, or is fixed on a lateral surface of the rotor.

4. The physiotherapy device according to claim 1, wherein each of the plurality number N of magnetic bodies is a Neodymium (NdFeB) magnet, a ferroferric oxide magnet, or a cobalt-nickel magnet.

5. The physiotherapy device according to claim 1, further comprising:
    a magnetic base is disposed in connection with the vibration capsule;
    the vibration capsule comprising
    a reed switch
    that cooperates with the magnetic base to turn on or turn off the vibration capsule;
    the reed switch is connected with the control panel electrically; and
    the reed switch located between the column-shaped vibration motor and the shell.

6. The physiotherapy device according to claim 1, wherein the shell is a biocompatibility shell.

7. The physiotherapy device according to claim 1, wherein the rotor is an eccentric rotor.

8. The physiotherapy device according to claim 7, wherein the eccentric rotor comprises a material having a density greater than 6-20 g/cm$^3$.

* * * * *